United States Patent [19]
Harris et al.

[11] Patent Number: 6,008,148
[45] Date of Patent: *Dec. 28, 1999

[54] OIL RESISTANT POLYBUTYLENE BASED HOT MELT ADHESIVE

[75] Inventors: Bonnie M. Harris, Wales; Monina Kanderski, Milwaukee, both of Wis.

[73] Assignee: Ato Findley, Inc., Wauwatosa, Wis.

[ * ] Notice: This patent issued on a continued prosecution application filed under 37 CFR 1.53(d), and is subject to the twenty year patent term provisions of 35 U.S.C. 154(a)(2).

[21] Appl. No.: 08/632,117

[22] Filed: Apr. 15, 1996

[51] Int. Cl.$^6$ ..................................... B32B 27/00
[52] U.S. Cl. ................. 442/381; 428/484; 428/500; 524/270; 524/275
[58] Field of Search .................. 442/381; 428/484, 428/500; 524/270, 275

[56] References Cited

U.S. PATENT DOCUMENTS

| | | | |
|---|---|---|---|
| 4,568,713 | 2/1986 | Hansen et al. | 524/291 |
| 4,826,909 | 5/1989 | Lakshmanan et al. | 524/478 |
| 4,833,192 | 5/1989 | Lakshmanan et al. | 524/476 |
| 4,937,138 | 6/1990 | Mostert | 428/286 |
| 4,956,207 | 9/1990 | Kauffman et al. | 428/34.2 |
| 5,021,257 | 6/1991 | Foster et al. | 427/2 |
| 5,024,888 | 6/1991 | Hwo et al. | 428/355 |
| 5,041,492 | 8/1991 | Koprowicz et al. | 524/274 |
| 5,106,447 | 4/1992 | Di Rado et al. | 156/334 |
| 5,254,612 | 10/1993 | Sugi et al. | 524/274 |
| 5,455,111 | 10/1995 | Velasquez Urey | 428/315.5 |

FOREIGN PATENT DOCUMENTS

| | | |
|---|---|---|
| 0331410 | 9/1989 | European Pat. Off. . |
| 90/00065 | 1/1990 | WIPO . |
| 92/12212 | 7/1992 | WIPO . |

*Primary Examiner*—Helen L. Pezzuto
*Attorney, Agent, or Firm*—Andrus, Sceales, Starke & Sawall

[57] ABSTRACT

A polybutylene based hot melt adhesive composition having a variety of end uses, particularly in construction and elastic attachment applications on nonwoven disposable articles. Unlike typical hot melt adhesives, the present composition can withstand exposure to mineral oil and other oil based ointments without experiencing catastrophic bond failure. The composition includes polybutylene copolymer or a mixture of polybutylene and polyolefin polymers, a tackifier resin, a plasticizer, a wax and a stabilizer. The hot melt adhesive composition can be applied using common application techniques such as extruding or spraying.

4 Claims, No Drawings

OIL RESISTANT POLYBUTYLENE BASED HOT MELT ADHESIVE

FIELD OF THE INVENTION

The present invention relates to hot melt adhesive compositions, and more particularly to an oil resistant polybutylene based hot melt adhesive which finds utility in construction and elastic attachment applications in nonwoven disposable absorbent articles such as diapers.

BACKGROUND OF THE INVENTION

Numerous types of nonwoven disposable absorbent articles are commercially available, and are manufactured for use in the absorption and containment of bodily waste such as urine and feces. Typical of such articles are disposable diapers for infants, and undergarments for incontinent adults. In the construction of such disposable articles, an inner leg gather or cuff is employed to prevent leakage of the bodily waste from around the user's legs. During use, this cuff or flap is held in place with one or more elastic bands surrounding the leg. These elastic bands are typically held in place and attached to the disposable article by a hot melt adhesive.

While a wide range of hot melt adhesive compositions are known and used in the construction of disposable articles, it is also well known that a hot melt adhesive used for bonding in a particular use or application may be completely unsuitable for other uses or applications. Thus, various hot melt adhesive compositions are used in the construction of disposable articles. For example, it is well known that polyolefin based hot melt adhesives are suitable for the construction of diapers, particularly in the bonding of polyethylene films, or the like, to tissue or nonwoven substrates in the production of such articles. However, it is also known that polyolefin based hot melt adhesives are not suitable for bonding of the elastic bands in the diapers because creep resistance is insufficient for such an application. For this reason, hot melt adhesives based on styrene such as styrene-isoprene-styrene (SIS) block copolymers or styrene-butadiene-styrene (SBS) block copolymers are used. These block copolymer adhesives, however, also possess shortcomings such as viscosity instability which manifests itself at elevated temperature.

Another shortcoming is that these block copolymers lose most of their bond strength upon exposure to mineral oil or other oil based ointments. Mineral oil and other oil based ointments are often used on infants to treat skin rashes, and thus prior hot melt adhesive compositions, upon exposure thereto, experience adhesive bond failure. As a result, the elastic leg bands may actually let loose from the diaper resulting in complete failure and break down of the inner leg cuff. Therefore, an adhesive that is capable of withstanding exposure to mineral oil or other oil based ointments while still providing sufficient bond strength for elastic band attachment in the inner leg cuff would be highly desirable.

Manufacturers of nonwoven disposable articles, such as diapers, would also prefer using only a single hot melt adhesive in the manufacture of such articles. Clearly, the use of two or more hot melt adhesives on the same article poses some problems such as different handling procedures, clean up procedures, etc. which the manufacturer would prefer to avoid. Therefore, a single adhesive that is capable of performing bonding functions in both construction applications as well as elastic attachment applications in nonwoven disposable articles would be highly desirable.

SUMMARY OF THE INVENTION

The present invention is directed to a hot melt adhesive composition which possesses certain physical properties that makes it ideally suited for use with nonwoven disposable articles. More particularly, the hot melt adhesive of the present invention maintains acceptable bond strength even after saturating exposure to mineral oil.

The hot melt adhesive composition of this invention can be particularly used in elastic attachment applications in disposable nonwoven articles such as diapers to bond various elastic materials to porous and nonporous substrates such as nonwoven, polyethylene, polypropylene, and the like to one another. The hot melt adhesive composition provides good elastic attachment bonds when tested via standard creep resistance test methods.

The hot melt composition of this invention also provides excellent construction bonds when tested via standard peel strength tests. In addition, when formulated for use with polyolefin films the hot melt adhesive maintains excellent dry bond strength even after exposure to elevated temperature aging, i.e. simulated warehouse conditions.

The hot melt adhesive composition of the present invention comprise a blend of the following:

(a) about 10% to 65% by weight of a polybutylene copolymer;
(b) about 0% to 65% by weight of a polyolefin copolymer;
(c) about 13% to about 60% by weight of a tackifying resin;
(d) about 0% to about 30% by weight of a plasticizer;
(e) about 0% to about 20% by weight of a wax; and
(f) about 0.1% to about 2% by weight of a stabilizer.

A preferred hot melt adhesive composition functioning either as a sprayable elastic attachment adhesive or as a construction adhesive while also providing adequate bond strength after oil exposure comprises a blend of the following:

(a) about 27.1% by weight of a polybutylene copolymer;
(b) about 27.1% by weight of a tackifying resin;
(c) about 36.1% by weight of a polyolefin copolymer;
(d) about 9.2% by weight of a wax; and
(e) about 0.5% by weight of a stabilizer.

A preferred hot melt adhesive composition functioning only as an elastic attachment adhesive while providing adequate bond strength after oil exposure comprises a blend of the following:

(a) about 63.2% by weight of a polybutylene copolymer;
(b) about 27.1% by weight of a tackifying resin;
(c) about 9.2% by weight of a wax; and
(d) about 0.5% by weight of a stabilizer.

The hot melt adhesive compositions of the present invention thus possess, depending upon the particular formulation, sufficient creep resistance to perform as an elastic attachment adhesive in a nonwoven disposable article, sufficient bond strength to perform as a construction adhesive in a nonwoven disposable article, maintenance of acceptable bond strength after oil exposure, and good peel adhesion to polyolefin after elevated temperature aging.

DETAILED DESCRIPTION OF THE PREFERRED EMBODIMENT

A polybutylene based hot melt adhesive composition having ingredients in the following ranges provides advantages over current technology when evaluated for retention of bond strength after oil exposure. More particularly, the adhesive composition includes about 10% to 65% by weight of polybutylene, or a mixture of polybutylene and polyolefin. Whether polybutylene is utilized alone or in a mixture of polybutylene and polyolefin, the minimum polymer content in the composition should be about 20% by weight. Depending on end use and desired properties, the polyolefin ingredient may be absent. Lack of the polyolefin component is particularly acceptable when the adhesive composition is used in an elastic attachment application. The hot melt adhesive composition of the present invention also includes about 13% to about 60% tackifying resin, about 0% to about 30% by weight plasticizer, about 0% to about 20% by weight wax, and about 0.1% to about 2% by weight stabilizer.

The polybutylene copolymer component is used in the thermoplastic hot melt adhesive of the present invention to enhance the strength of the adhesive bond of the material at elevated temperatures, which is necessary for elastic attachment applications, and to provide oil resistance to the composition. As used herein, the term "polybutylene copolymer" refers to those polymeric entities comprised of ethylene and butene monomers where the butene monomeric unit comprises at least 89% of the copolymer. These are available from the Shell Chemical Co. under the trade name "Duraflex." A suitable commercially available butene-1-ethylene copolymer can be secured from Shell Chemical Company of Houston, Tex. under the tradename Duraflex 8910 PC or Duraflex 8510. The preferred materials have a Ring and Ball softening point of approximately 150° C. (302° F.). Although a range of 10–65% by weight polybutylene copolymer may be used, the preferred range is 20% to 45%.

Butene-1-homopolymers and copolymers which are useful in the present invention are primarily linear chain molecules with regular and spatially ordered arrangements of ethyl side groups. These side groups are the result when butene-1 is polymerized across the 1, 2, carbon double bond, and along an ethylene chain backbone. This is described in further detail in U.S. Pat. No. 3,362,940. When cooled from a melt, the ethyl side groups initially align in a tetragonal spatial arrangement. With time the tetragonal crystalline phase form transfers into a stable hexagonal spatial arrangement with a subsequent development of improved physical properties. A more thorough discussion of the polymer utilized herein may be found in the reference to Mostert, U.S. Pat. No. 4,937,138, the contents of which is incorporated by reference herein. As will be seen from the disclosure above, the present polymer is useful in amounts of about 10% to about 65%, by weight.

The amorphous copolyolefin copolymer component, i.e. the polyalphaolefin copolymer, of the composition of the present invention is a copolymer based on repeating units of ethylene, propylene and butene. They may be comprised of alternating repeating units of the following monomer combinations:

(a) Ethylene and propylene
(b) Ethylene and butene
(c) Propylene and butene
(d) Ethylene, propylene and butene Suitable copolymers are commercially available from Huls America under the trade name "Vestoplast." Those with a softening point of about 300° F. (149° C.) are preferred. It will be recognized that mixtures of any of the above copolymers also may be used as base components in the compositions of the present invention. The polyalphaolefin copolymer functions to provide adhesion to nonporous substrates. Although a range of 0–65% by weight polyalphaolefin copolymer may be used, the preferred range is 20% to 40%.

It should be noted that mixtures of the polybutylene copolymer and polyalphaolefin copolymer may also be used as long as a sufficient amount of polybutylene copolymer is employed to impart the desired amount of creep resistance to the adhesive composition. The minimum polymer content in the composition should be about 20%. Thus, depending on the end use, and as noted above, the polyalphaolefin component could be absent from the composition.

The tackifying resins which are used in the hot melt construction adhesives of the present invention are those which extend the adhesive properties and improve the specific adhesion of the polybutylene copolymer and/or the polyalphaolefin copolymer. As used herein, the term "tackifying resin" includes:

(a) natural and modified rosin such as, for example, gum rosin, wood rosin, tall-oil rosin, distilled rosin, hydrogenated rosin, dimerized rosin and polymerized rosin;

(b) glycerol and pentaerythritol esters of natural and modified rosins, such as, for example, the glycerol ester of pale wood rosin, the glycerol ester of hydrogenated rosin, the glycerol ester of polymerized rosin, the pentaerythritol ester of pale wood rosin, the pentaerythritol ester of hydrogenated rosin, the pentaerythritol ester of tall oil rosin and the phenolic modified pentaerythritol ester of rosin;

(c) polyterpene resins having a softening point, as determined by ASTM method E28-58T, of from about 60° C. to 140° C., the latter polyterpene resins generally resulting from the polymerization of terpene hydrocarbons, such as the mono-terpene known as pinese, in the presence of Friedel-Crafts catalysts at moderately low temperatures; also included are the hydrogenated polyterpene resins;

(d) copolymers and terpolymers of natural terpenes, e.g. styrene/terpene, α-methyl styrene/terpene and vinyl toluene/terpene;

(e) phenolic-modified terpene resins such as, for example, the resin product resulting from the condensation, in an acidic medium, of a terpene and a phenol;

(f) aliphatic petroleum hydrocarbon resins having Ring and Ball softening points of from about 60° to 140° C., the latter resins resulting from the polymerization of monomers consisting primarily of olefins and diolefins; also included are the hydrogenated aliphatic petroleum hydrocarbon resins; examples of such commercially available resins based on a $C_5$-olefin fraction of this type are "Wingtack 95" and "Wingtack 115" tackifying resins sold by Goodyear Tire and Rubber Company;

(g) aromatic petroleum hydrocarbons and the hydrogenated derivatives thereof;

(h) aliphatic/aromatic petroleum derived hydrocarbons and the hydrogenated derivatives thereof.

Mixtures of two or more of the above described tackifying resins may be required for some formulations. Although a range of 13–60% by weight tackifying resin may be used, the preferred range is 20% to 50%.

As noted above, tackifying resins which are useful within the scope of the present invention comprise about 13% to about 60% by weight. The tackifying resins can be selected from any of the nonpolar types, which are commercially available. An example of a commercially available tackifying resin which is useful for the present invention includes the resin which is identified commercially by the trade designation Escorez 5300 and which is manufactured by Exxon Chemical Company. Normally, nonpolar tackifying resins which are useful with the present invention include resins which have partially, or completely hydrogenated $C_9$ or $C_5$ based hydrocarbon resins with softening points that are in a range of approximately 70° C. to approximately 125° C. Tackifying resins which are useful for the present invention can perhaps include polar tackifying resins, however, the choice of available polar tackifying resins is limited in view of the fact that many of the polar resins appear only partially compatible with the butene-1-homopolymer, and copolymers.

A plasticizer can be present in the composition of the present invention in amounts of about 0% to about 30%, by weight, preferably from about 5% to about 15%, in order to provide desired viscosity control. A suitable plasticizer may be selected from the group which includes the usual plasticizing oils, such as mineral oil, but also olefin oligomers and low molecular weight polymers, as well as vegetable and animal oil and derivatives of such oils. The petroleum derived oils which may be employed are relatively high boiling temperature materials containing only a minor proportion of aromatic hydrocarbons. In this regard, the aromatic hydrocarbons should preferably be less than 30%, more particularly less than 15%, by weight, of the oil. Alternately, the oil may be totally non-aromatic. The oligomers may be polypropylenes, polybutenes, hydrogenated polyisoprene, hydrogenated butadiene, or the like having average molecular weights between about 350 and about 10,000. Suitable vegetable and animals oils include glycerol esters of the usual fatty acids and polymerization products thereof. The plasticizer that finds usefulness in the present invention can be any number of different plasticizers but the inventors have discovered that a plasticizer which includes a mono-olefin polymer such as what is commercially available under the trade designation Indopol H-100, and which is manufactured by Amoco, is particularly useful in the present invention. As will be appreciated, plasticizers have typically been employed to lower the viscosity of the overall adhesive composition without substantially decreasing the adhesive strength and/or the service temperature of the adhesive.

The waxes which can be used in amounts varying between 0% to 20% by weight, preferably 5% to 15%, in the composition of the present invention are used to reduce the melt viscosity of the hot melt construction adhesives without appreciably decreasing their adhesive bonding characteristics. These waxes also to reduce the open time of the composition without effecting the temperature performance. Among the useful waxes are:

(1) low molecular weight, that is, 1000–6000, polyethylene having a hardness value, as determined by ASTM method D-1321, of from about 0.1 to 120 and ASTM softening points of from about 150° to 250° F.;

(2) petroleum waxes such as paraffin wax having a melting point of from about 130° to 175° F. and microcrystalline wax having a melting point of from about 135° to 200° F., the latter melting points being determined by ASTM method D127-60;

(3) atactic polypropylene having a Ring and Ball softening point of from about 120° to 160° C.;

(4) synthetic waxes made by polymerizing carbon monoxide and hydrogen such as Fischer-Tropsch wax; and (5) polyolefin waxes. As used herein, the term "polyolefin wax" refers to those polymeric or long-chain entities comprised of olefinic monomer units. These materials are commercially available from Eastman Chemical Co. under the trade name "Epolene." The materials which are preferred for use in the compositions of the present invention have a Ring and Ball softening point of 200° F. to 350° F. As should be understood, each of these wax diluents is solid at room temperature. Other useful substances include hydrogenated animal, fish and vegetable fats and oils such as hydrogenated tallow, lard, soya oil, cottonseed oil, castor oil, menhadin oil, cod liver oil, etc., and which are solid at ambient temperature by virtue of their being hydrogenated, have also been found to be useful with respect to functioning as a wax diluent equivalent. These hydrogenated materials are often referred to in the adhesives industry as "animal or vegetable waxes." Additionally, hydrocarbon oils, especially naphthenic or paraffinic process oils, may also be employed herein as the wax diluent.

The present invention includes a stabilizer in an amount of from about 0.1% to about 2% by weight, but preferably from about 01.% to 1%. The stabilizers which are useful in the hot melt adhesive compositions of the present invention are incorporated to help protect the polymers noted above, and thereby the total adhesive system, from the effects of thermal and oxidative degradation which normally occurs during the manufacture and application of the adhesive as well as in the ordinary exposure of the final product to the ambient environment. Such degradation is usually manifested by a deterioration in the appearance, physical properties and performance characteristics of the adhesive. Among the applicable stabilizers are high molecular weight hindered phenols and multifunctional phenols, such as sulfur and phosphorous-containing phenols. Hindered phenols are well known to those skilled in the art and may be characterized as phenolic compounds which also contain sterically bulky radicals in close proximity to the phenolic hydroxyl group thereof. In particular, tertiary butyl groups generally are substituted onto the benzene ring in at least one of the ortho positions relative to the phenolic hydroxyl group. The presence of these sterically bulky substituted radicals in the vicinity of the hydroxyl group serves to retard its stretching frequency and correspondingly, its reactivity; this steric hindrance thus providing the phenolic compound with its stabilizing properties. Representative hindered phenols include:

1,3,5,-trimethyl-2,4,6-tris(3-5-di-tert-butyl-4-hydroxybenzyl) benzene;

pentaerythritol tetrakis-3(3,5-di-tert-butyl-4-hydroxyphenyl) propionate;

n-octadecyl-3(3,5-di-tert-butyl-4-hydroxyphenyl) propionate;

4,4'-methylenebis(4-methyl-6-tert butylphenol);

4,4'-thiobis(6-tert-butyl-o-cresol);

2, 6-di-tert-butylphenol;

6- (4-hydroxyphenoxy)-2,4-bis(n-ocytlthio)-1,3,5-triazine;

2,4,6-tris(4-hydroxy-3,5-di-tert-butyl-phenoxy)-1,3,5-triazine;

di-n-octadecyl-3,5-di-tert-butyl-4-hydroxybenzylphosphonate;

2-(n-octylthio)ethyl-3,5-di-tert-butyl-4-hydroxybenzoate; and sorbitol hexa-(3,3,5-di-tert-butyl-4-hydroxy-phenyl) propionate.

Especially preferred as a stabilizer is pentaerythritol tetrakis-3(3,5-di-tert-butyl-4-hydroxyphenol) propionate.

The performance of these stabilizers may be further enhanced by utilizing, in conjunction therewith; (1) synergists such as, for example, as thiodipropionate esters and phosphites; and (2) chelating agents and metal deactivators as, for example, ethylenediaminetetraacetic acid, salts thereof, and disalicylalpropylenediimine.

The hot melt adhesive composition of the present invention may be formulated using any of the techniques known in the art. A representative example of the prior art procedure involves placing all of the substances, in a jacketed mixing kettle, and preferably in a jacketed heavy duty mixer of the Baker-Perkins or Day type, and which is equipped with rotors, and thereafter raising the temperature of this mixture to a range of about 250° F. to 350° F. It should be understood that the precise temperature to be used in this step would depend on the melting point of the particular ingredients. The resulting adhesive composition is agitated until the polymers completely dissolve. A vacuum is then applied to remove any entrapped air.

It should be understood that other optional additives may be incorporated into the adhesive composition of the present invention in order to modify particular physical properties. These may include, for example, such materials as colorants, fillers, etc.

The invention is further illustrated by way of the examples which are set forth below.

EXAMPLE 1

The following adhesive blend was prepared in accordance with the present invention. When tested (see EXAMPLES 5–7), the adhesive performed exceptionally well as either an elastic attachment adhesive or as a construction adhesive while also providing adequate bond strength after oil exposure.

| Weight % | Ingredient | Commercial Source | Generic Name |
|---|---|---|---|
| 27.1 | Escorez 5300 | Exxon Chemical Company | resin |
| 27.1 | Duraflex 8910PC | Shell Chemical Company | polybutylene |
| 36.1 | Vestoplast 708 | Huls America, Incorporated | polyolefin |
| 9.2 | Epolene N15 | Eastman Chemical Products | wax |
| 0.5 | Irganox 1010 | Ciba Additives | stabilizer |

EXAMPLE 2

The following adhesive blend was prepared in accordance with the present invention. When tested (see EXAMPLES 5–7), the adhesive performed exceptionally well as either an elastic attachment adhesive or as a construction adhesive while also providing adequate bond strength after oil exposure.

| Weight % | Ingredient | Commercial Source | Generic Name |
|---|---|---|---|
| 24.9 | Escorez 5300 | Exxon Chemical Company | resin |
| 24.9 | Duraflex 8910PC | Shell Chemical Company | polybutylene |
| 33.2 | Vestoplast 708 | Huls America, Incorporated | polyolefin |
| 16.6 | Epolene N15 | Eastman Chemical Products | wax |
| 0.4 | Irganox 1010 | Ciba Additives | stabilizer |

EXAMPLE 3

The following adhesive blend was prepared in accordance with the present invention. When tested (see EXAMPLES 6–7), the adhesive performed exceptionally well as an elastic attachment adhesive while also providing adequate bond strength after oil exposure.

| Weight % | Ingredient | Commercial Source | Generic Name |
|---|---|---|---|
| 27.1 | Escorez 5300 | Exxon Chemical Company | resin |
| 63.2 | Duraflex 8910PC | Shell Chemical Company | polybutylene |
| 9.2 | Epolene N10 | Eastman Chemical Products | wax |
| 0.5 | Irganox 1010 | Ciba Additives | stabilizer |

EXAMPLE 4

The following adhesive blend was prepared in accordance with the present invention. When tested (see EXAMPLE 6), the adhesive performed exceptionally well as an elastic attachment adhesive. As the formulation of this example is similar to EXAMPLES 1 and 2, it would be expected that this formulation would also perform well as a construction adhesive while also providing adequate bond strength after oil exposure.

| Weight % | Ingredient | Commercial Source | Generic Name |
|---|---|---|---|
| 27.1 | Escorez 5300 | Exxon Chemical Company | resin |
| 40.7 | Duraflex 8910PC | Shell Chemical Company | polybutylene |
| 22.6 | Vestoplast 708 | Huls America, Incorporated | polyolefin |
| 9.2 | Epolene N10 | Eastman Chemical Products | wax |
| 0.5 | Irganox 1010 | Ciba Additives | stabilizer |

EXAMPLE 5

Test Method: Laminations were made with two elastic strands (Lycra) stretched 250% between two layers of nonwoven. Adhesive was spiral sprayed at 10 mg/in$^2$ with a 0.25 second open time. Application temperature was 365° F. for the adhesive, and 400° F. for the air. Laminations were tested dry, and after saturating them with mineral oil and aging 90 minutes at 100° F. Test mode was a 180° peel at 12°/minute. Maximum load is reported in grams/inch.

Control: A commercially available elastic attachment adhesive containing a styrenic block copolymer and various resins and plasticizers. The control adhesive contains no polybutylene, and is available from Ato Findley, Inc. under the trade designation H2096.

TABLE 1

| | NW/NW Crossdirectional Peel | |
|---|---|---|
| | Peak Peel-Dry [grams/inch] | Peak Peel-Oiled [grams/inch] |
| Control | 768 | 2 |
| Example 1 | 818 | 172 |
| Example 2 | 776 | 232 |

Conclusion: Control sample falls apart after oil saturation, which would allow elastic strands to escape in the finished article. Examples 1 and 2 maintain sufficient bond strength after oil saturation to prevent the elastic strands from escaping. Preferably, under these test conditions, it is believed the peel strength should be about 75 grams/inch or greater after oil emersion in order to provide adequate performance.

EXAMPLE 6

Test Method: Laminations were made as above in EXAMPLE 5. The control, Examples 1 and 2 were coated between two layers of nonwoven. Examples 3 and 4 were coated between nonwoven and treated polyethylene. Samples were partially stretched and fastened to a board. (Samples were extended fully, a 200 mm length was measured, then relaxed and fixed at 150 mm.) The elastic strands were cut, marked, and measured. After aging 90 minutes at 100° F., the elastic strands were remeasured and compared to their original length.

$$\frac{\text{New Length}}{\text{Old Length}} \times 100 = \% \text{ Retention}$$

TABLE 2

| | Creep Resistance (% Retention) |
|---|---|
| Control | 96 |
| Example 1 | 91 |
| Example 2 | 92 |
| Example 3 | 94 |
| Example 4 | 87 |

Conclusion: Comparison of the Examples to the traditional Control product demonstrates that the products of the present invention have acceptable performance under standard test conditions. Under these test conditions, unacceptable creep resistance would be 80% or less.

EXAMPLE 7

This example is designed to simulate warehouse storage conditions.

Test Method: Nonwoven was laminated to polyethylene with a single bead of adhesive applied at 5 mg/lineal inch. Application temperature was 325° F. with a 0.25 second open time. Samples were tested initially after aging 1 week at 130° F. Test mode was a 180° peel at 12"/min. Maximum load is reported in grams/inch.

TABLE 3

| | Poly/NW Crossdirectional Peel [grams/inch] | |
|---|---|---|
| | Initial | Aged |
| Control | 533 | 600 |
| Example 1 | 576 | 463 |
| Example 2 | 470 | 422 |
| Example 3 | 734 | 61 |

Conclusion: Test results show that a properly formulated adhesive can be used not only for oil resistant lamination of nonwoven, but other construction applications requiring stable adhesion to polyethylene. Example 3 demonstrates that not all Polybutylene based adhesives would work for both elastic attachment and constructions applications, i.e. the formulation of Example 3 is useful as an elastic attachment adhesive but not as a construction adhesive in a nonwoven disposable article such as a diaper.

I claim:

1. An oil resistant hot melt adhesive composition consisting of a blend of:
   (a) about 10% to about 65% by weight of a polybutylene homopolymer, copolymer or blends thereof;
   (b) about 13% to about 60% by weight of a nonpolar tackifying resin, said nonpolar tackifying resin selected from the group consisting of polyterpene resins, hydrogenated polyterpene resins, copolymers of natural terpenes, terpolymers of natural terpenes, phenolic-modified terpene resins, aliphatic hydrocarbon resins, hydrogenated aliphatic hydrocarbon resins, aromatic hydrocarbon resins, hydrogenated aromatic hydrocarbon resins, and mixtures thereof;
   (c) about 0% to about 30% by weight of a plasticizer;
   (d) about 6% to about 20% by weight of a wax; and
   (e) about 0.1% to about 2% by weight of a stabilizer, wherein the minimum polymer content is 20% by weight, said composition having a peel strength of about 75 grams/inch or greater after saturating a lamination of said composition with mineral oil and aging 90 minutes at 100° F. as determined by a 180° peel at 12 inches/minute, said lamination composed of a pair of elastic strands stretched 250% between two layers of nonwoven sheets with the adhesive composition spiral sprayed at 10 mg/in² therebetween at an application temperature of 365° F.

2. An oil resistant hot melt adhesive composition as claimed in claim 1, and wherein the plasticizer is selected from the group consisting of mineral oil and low molecular weight polybutene, said polybutene having an average molecular weight in the range of about 350 to 10,000.

3. An oil resistant hot melt adhesive composition, consisting of:
   (a) about 20% to about 45% by weight of a polybutylene homopolymer, copolymer or blends thereof;
   (b) about 20% to about 50% by weight of a nonpolar tackifying resin, said nonpolar tackifying resin selected from the group consisting of polyterpene resins, hydrogenated polyterpene resins, copolymers of natural terpenes, terpolymers of natural terpenes, phenolic-modified terpene resins, aliphatic hydrocarbon resins, hydrogenated aliphatic hydrogenated resins, aromatic hydrocarbon resins, hydrogenated aromatic hydrocarbon resins, and mixtures thereof;
   (c) about 6% to about 15% by weight of a wax; and
   (d) about 0.1% to about 1% by weight of a stabilizer, said composition having a peel strength of about 75 grams/inch or greater after saturating a lamination of said composition with mineral oil and aging 90 minutes at 100° F. as determined by a 180° peel at 12 inches/minute, said lamination composed of a pair of elastic strands stretched 250% between two layers of nonwoven sheets with the adhesive composition spiral sprayed at 10 mg/in² therebetween at an application temperature of 365° F.

4. An oil resistant hot melt adhesive composition as claimed in claim 3, and wherein the plasticizer is selected from the group consisting of mineral oil and low molecular weight polybutene, said polybutene having an average molecular weight in the range of about 350 to 10,000.

* * * * *